United States Patent [19]
Letcher

[11] Patent Number: 5,971,760
[45] Date of Patent: Oct. 26, 1999

[54] METHOD OF INSTALLING A REPLACEMENT OF A PATIENT'S DETERIORATED TOOTH

[76] Inventor: William F. Letcher, 5522 S. Lewis, Tulsa, Okla. 74105

[21] Appl. No.: 09/207,885

[22] Filed: Dec. 8, 1998

Related U.S. Application Data

[63] Continuation-in-part of application No. 09/032,590, Feb. 27, 1998, Pat. No. 5,876,209.

[51] Int. Cl.$^6$ ..................................................... A61C 5/10
[52] U.S. Cl. ........................................... 433/223; 433/220
[58] Field of Search ................................... 433/213, 218, 433/219, 223, 229, 220

[56] References Cited

U.S. PATENT DOCUMENTS

| | | | |
|---|---|---|---|
| 5,475,912 | 12/1995 | Sundstrom | 433/223 X |
| 5,490,810 | 2/1996 | Hahn et al. | 433/223 X |
| 5,593,305 | 1/1997 | Shoher et al. | 433/223 X |
| 5,624,263 | 4/1997 | Babian | 433/223 |
| 5,735,692 | 4/1998 | Berger | 322/223 X |

*Primary Examiner*—Nicholas D. Lucchesi
*Attorney, Agent, or Firm*—Head Johnson & Kachigian

[57] ABSTRACT

The method of manufacturing a dental crown for use in replacing a deteriorated tooth includes the steps of making an impression of the patient's teeth including the deteriorated tooth and then making a first model from the impression. The deteriorated tooth is then extracted and a dental post installed in its place. An impression is made of the patient's teeth with the dental post and from this impression a second model is made. By use of heat and pressure a thin plastic foil is applied over the second model. By use of heat and pressure a thicker plastic foil form is made from the first model. Moldable crown forming material is then placed on the plastic foil encapsulated prepared tooth on the second model. The plastic foil form is then placed over the foil covered second mold to shape the moldable crown forming material. The crown forming material is then hardened to create a crown that is removed from off of the foil covered second model and out of the plastic foil form. The created crown is then further hardened and polished as necessary and can then be cemented onto the implanted dental post.

10 Claims, 7 Drawing Sheets

METHOD OF INSTALLING A REPLACEMENT OF A PATIENT'S DETERIORATED TOOTH

REFERENCE TO APPLICATIONS

This application is a continuation-in-part of U.S. patent application Ser. No. 09/032,590, filed Feb. 27, 1998, entitled "METHOD OF MANUFACTURING A DENTAL CROWN now U.S. Pat. No. 5,876,209."

REFERENCE TO MICROFICHE APPENDIX

This application is not referenced in any microfiche appendix.

BACKGROUND OF THE INVENTION

For many years dentistry has enhanced the quality of life of mankind by providing crowns for damaged, decayed or disfigured teeth. When a tooth is partially broken off, is disfigured caused by discoloration or has been damaged by decay, a modern dentist can restore the tooth both in function and appearance to a desired external shape by applying a crown. As commonly practiced today, a dentist first takes an impression employing a plastic material of the patient's teeth, typically an impression will include all of the patient's upper teeth or all of the patient's lower teeth. From such impression a mold is easily made by filling the impression with plaster that hardens and, after hardening, is easily removable from the soft plastic mold to faithfully replicate a patient's upper or lower teeth, including the adjacent gum areas. The dentist then prepares the damaged tooth to receive a crown by removing external portions, that is by grinding away external parts to reduce the total dimensional size of the tooth to be crowned so that all exterior portions thereof are confined within an area less than that of the desired crown. After the tooth has been prepared by removing exterior portions, a second impression is taken from which a second plaster mold is made.

These plaster molds are then sent off to a dental laboratory where a laboratory technician can manufacture a crown. After the crown is completed it is returned to the dentist who then cements it in place on the patient's prepared tooth.

This procedure works satisfactorily except that it takes several days up to several weeks from the time the dentist makes the impressions until the crown is returned to the dentist for installation in the patient's mouth. Typically when a tooth is prepared to receive a crown it is very visually distractive. To enable a patient to function both physically, that is to masticate food, and to function socially, that is to have a reasonable appearance, the typical procedure is that the dentist forms a temporary crown by molding temporary crown forming material on the prepared tooth and shaping it and hardening it in the patient's mouth so that hopefully the temporary crown will last until the crown to be formed in the dental laboratory is ready for installation.

Preparing a temporary crown has been a problem in the dental profession for many years since such temporary crowns frequently break or dislodge before the patient returns to the dental office to receive the permanent crown. Further and of even more significance is that the total procedure presently employed for crowning a tooth is time consuming on the part of the dentist and on the part of the patient since it requires the patient to make two separate visits to the dental office. The current procedure that requires a dentist to perform all of the dental work in his office whereas the crown itself is manufactured at a remote location not only creates inefficiency but adds to the expense. The primary problem, however, in today's dentistry with the crowning of a tooth is the inconvenience to the patient and the time constraints placed on the dentist. Further, problems with temporary crowns have always been a concern to dentists.

A method will be described herein in which a dentist can, with a single office visit by a patient, provide the patient a permanent crown. Stating it another way, a basic objective of the invention herein is a method of preparing a tooth and installing on the prepared tooth a permanent crown that can be done by a dentist entirely within his dental office.

BRIEF SUMMARY OF THE INVENTION

This invention provides a method for making a crown for a patient's tooth in which a dentist can provide a precisely fitted crown of utmost quality during a reasonably short single visit by a patient to the dentist office and without the necessity to resort to the use of a dental laboratory or other outside facility.

When a patient requiring a crown appears at the dentist office, the first step performed by the dentist is to take an impression of the patient's teeth, that is, either the upper teeth or lower teeth according to the location of the tooth requiring the crown. The impression is taken in the usual manner as followed by dentists for many years in which a soft plastic material having the ability to conform to the shape of a patient's teeth is placed in a form and pressed against the teeth to surround the teeth to the gum level. While the only portion of the impression that will be important is the tooth to be crowned and the teeth adjacent to it, for all practical purposes, it is easiest for the dentist to make an impression of the patient's full upper or lower teeth.

After the impression, a liquid plastic slurry is poured into the impression and allowed to solidify to provide a model that replicates the patient's upper or lower teeth. This model is referred to as a "first model".

If the tooth in its natural state, that is, when the impression is made that has exterior defects, the dentist applies sculpturing material to fill in such defects and otherwise reshape the tooth on the first mold to that which will be ideal for the external appearance of the crown when completed. Material for sculpturing the tooth on the model can then be hardened as necessary so that the sculptured tooth presents an external shape that is the desired external shape of the crown to be created.

The dentist then structures the patient's tooth to receive the crown by grinding away surface portions to provide a tooth base, that is, the patient's tooth is structurally configured to receive and support a crown. If the crown is to be a full crown, that is to completely surround the remaining natural tooth then exterior portions substantially around the entire tooth are removed so that the crown, when installed, will uniformly circumscribe and cover the entire remaining tooth structure. The grinding away of exterior portions of the tooth to be crowned results in a prepared tooth.

The dentist then makes a second impression of the patient's tooth including the prepared tooth, and from the second impression, by the use of plaster, a second model is made which replicates the patient's teeth, the second model being differed from the first model in that the tooth to be crowned has been changed by the dentist in the process of creating the prepared tooth.

The dentist then applies an acrylic releasing plastic foil over the first model. In this step plastic foil is heated and air pressure applied to cause it to conform to the prepared first model to obtain an external crown form, that is, a form having a cavity therein that defines the external appearance of the crown to be formed. The external crown form made by the plastic foil is removed from the first model.

The dentist then places a thin acrylic releasing plastic foil over the second model. By "acrylic releasing" is meant a foil that has the characteristic that acrylic material used to form a crown does not adhere to it, that is, wherein the formed acrylic that makes the crown is readily releasable from the foil material. The thin acrylic releasing plastic foil is heated and air pressure is applied to it to cause it to conform to and encompass the second model.

The dentist then places moldable crown forming material on the plastic foil encapsulated prepared tooth on the second model. While the moldable crown forming material is still in plastic state, the dentist then places the external crown form over the foil covered second mold to cause the moldable crown forming material thereon to simultaneously take an internal contour matching the shape of the prepared tooth and an external contour matching the shape of the sculptured tooth. The moldable crown forming material is then hardened, a step that can be accomplished very successfully by applying ultraviolet light to the molded crown forming material. The moldable crown forming material preferably is a polymer glass ceramic specifically formulated to remain plastic until subjected to high intensity ultraviolet light.

After the ceramic forming material has solidified, the crown can then be removed from off of the foil covered second mold and out of the external crown form. Any surplusage surrounding the crown can be ground away and the crown polished. The crown is then ready to be cemented in place on the patient's prepared tooth.

The total procedure can be carried out expeditiously during a one time patient visit to the dentist office so that the patient, when leaving the dentist office, will have a permanently mounted crown rather than, with the current procedure, a temporary crown. The steps outlined above are not necessary practice in the specific order enumerated.

In the step of placing crown forming material over the foil covered second mold, the dentist may do this in steps, that is, by placing a small amount of crown forming material on the plastic foil encapsulated prepared tooth and then hardening the material before placing additional layers since hardening by the use of ultraviolet light can be most effectively accomplished when the crown forming material is not unduly thick thereby permitting more effective penetration by the ultraviolet light. The only requirement is that the outer layer of crown forming material must still be in a plastic state when the final external crown form is placed on the second model so that the moldable material will conform to the external crown form.

A better understanding of the invention will be obtained from the following description of the preferred embodiments and claims, taken in conjunction with the attached drawings.

DETAILED DESCRIPTION OF THE PREFERRED EMBODIMENTS

When a patient comes to a dentist requiring a tooth to be crowned, the dentist first obtains an impression of either the upper teeth or lower teeth that contains the tooth to be crowned. This step is not illustrated in the drawings since it is a step that has long been practiced by dentists and is a familiar procedure to any person who has had a crown, bridge or other restorative dentistry. The impression is formed by placing a soft pliable material into a holder shaped to accommodate the upper or lower teeth of a patient. After the holder having the impression material therein is pressed around the teeth, it is removed and a slurry of model forming material, such as plaster, is poured into the impression. Plaster is the most commonly used material in dentistry for forming a model. Plaster is desirable because of its convenience, economy and the fact that it sets up rapidly. This step results in providing a model of the patient's teeth which includes the teeth to be crowned hereinafter referred to as a first model.

Figure 1:
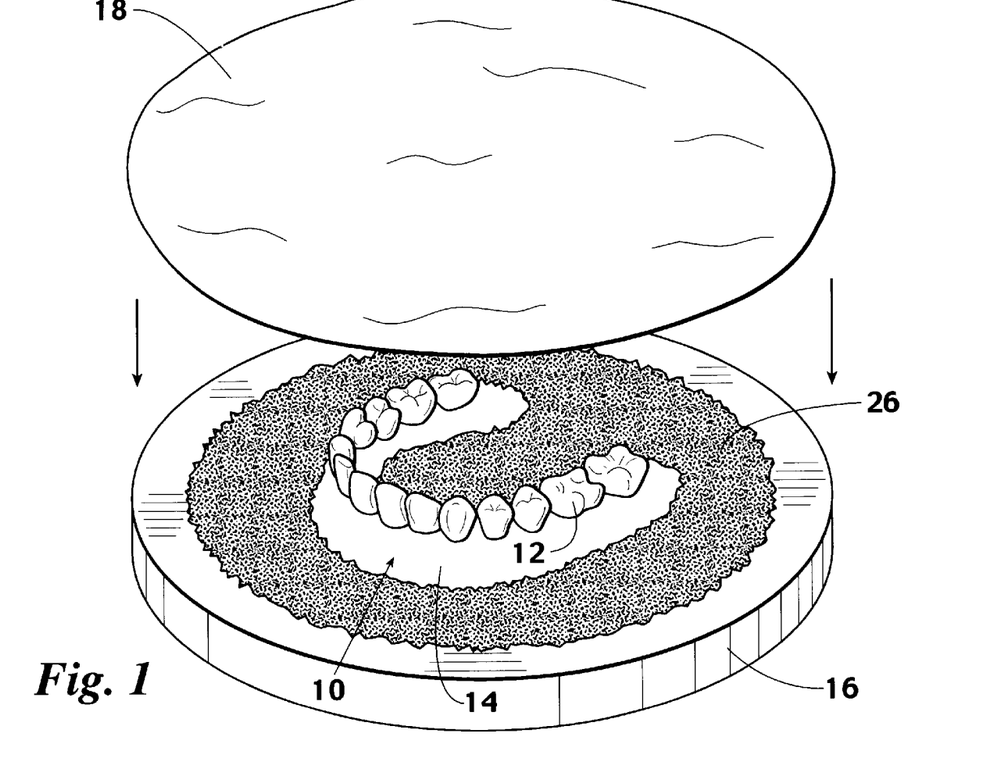
FIG. 1 is an isometric view showing a model that has been made of an impression taken of a patient's lower teeth, the model showing a molar to be crowned. The model is shown positioned in a receptacle that is part of a machine (not shown) by which heat and pressure is applied to a circular sheet of plastic foil.

FIG. 1 shows a first model, generally indicated by the numeral 10, of a patient's teeth. Model 10 is, as previously indicated, typically of solidified plaster and includes a tooth 12, a molar in this case, that requires a crown. The model includes some of the gum portion 14 of the patient's tooth supporting structure.

In creating a crown it is normally desirable that the finished crown will have a shape substantially that of the normal tooth before the tooth is prepared to receive the crown. It is normally desirable in the formation of a crown to be placed on a prepared tooth for the crown to have a configuration substantially similar to the normal tooth of the patient before the dentist has done preparatory work on the tooth. However, many teeth and particularly ones requiring crowns may have defects in their exterior appearance, such as teeth having portions that have been broken away or have deteriorated. For this reason, after model 10 has been made from an impression the dentist may apply molding material to tooth 12 to reconfigure and shape it to eliminate imperfections and to create a model in which the tooth has the external appearance of the crown to be created. Tooth 12 of first model 10 as shown in FIG. 1 has been sculptured as required by the dentist so that it appears substantially identical to the desired external appearance of the finished crown.

Figure 2:
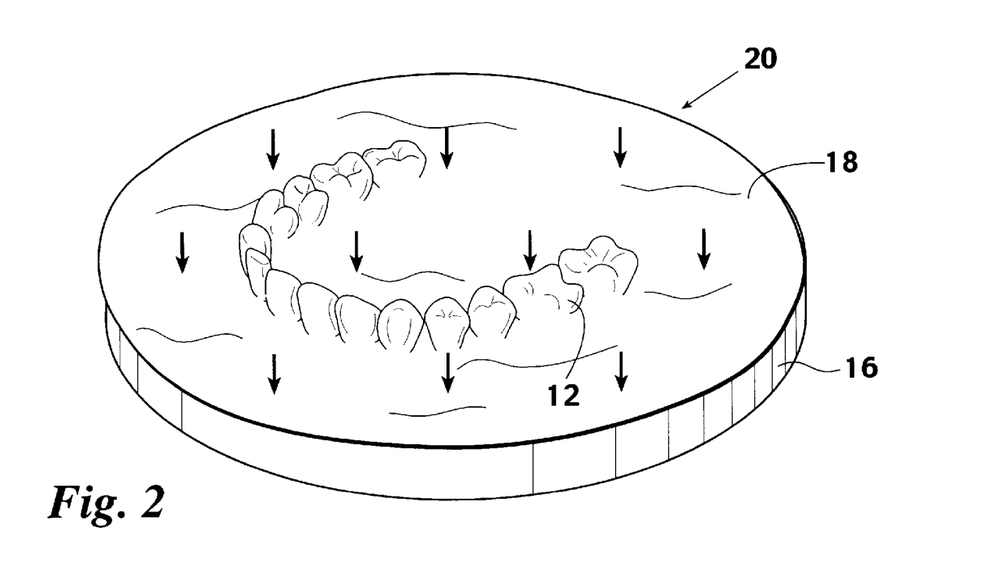
FIG. 2 shows the model of FIG. 1 after it has been encapsulated by the sheet of plastic foil. The plastic foil creates an external crown form defining the exterior configuration of a crown to be manufactured.

The next step illustrated in the drawing, as indicated by FIG. 1, is to obtain a form replicating model 10. This can be accomplished utilizing readily commercially available equipment, such as manufactured by Scheu-Dental of Iserlohn, Germany and sold under the trademark "BIO-STAR". This equipment includes a platform (not seen in FIG. 1 but shown in FIG. 3) on which first model 10 rests in a container positioned within a housing that support structure by which a plastic foil is heated and subjected to air pressure to cause the plastic foil to form around first model 10 as seen in FIG. 2. FIG. 2 shows the plastic foil 18 having been heated and forced by air pressure to closely adhere to the external configuration of the first model 10 to provide a plastic form indicated by the numeral 20, the plastic form 20 being the plastic foil 18 after it has been heated and conformed by air pressure to the external shape of the patient's teeth including the tooth to receive the crown.

Plastic foil 18 is available from Scheu-Dental and is sold under the trademark "COPYPLAST". It is a tough plastic clear foil that does not bond to acrylic or ceramic forming molding compositions as employed herein. Plastic foil 18 is heated by use of ultraviolet light to a temperature of typically about 420° F., which requires typically about one minute, after which air pressure is applied above the heated film to force it down over and around the teeth replicated in first model 10, requiring only a few seconds.

After the plastic foil 18 has cooled, taking only a minute or so, the air pressure can be released and the plastic foil covered first model removed from the machine. The foil form 20 is easily removed from the model and is used in making a crown as will be explained subsequently. Therefore, in FIG. 2 the finished form 20 has the external shape of the desired external configuration of a finished crown.

Next the dentist then shapes the patient's natural tooth to be crowned in a way to provide a prepared tooth, that is a tooth that is conditioned to receive a crown. This is accomplished by removing exterior portions of the tooth. Exterior portions of the natural tooth must be removed sufficient so that the crown will have thickness to give it strength while, at the same time, the prepared tooth must have as much of the natural tooth remaining as is necessary to provide structural support for the crown.

Figure 3:
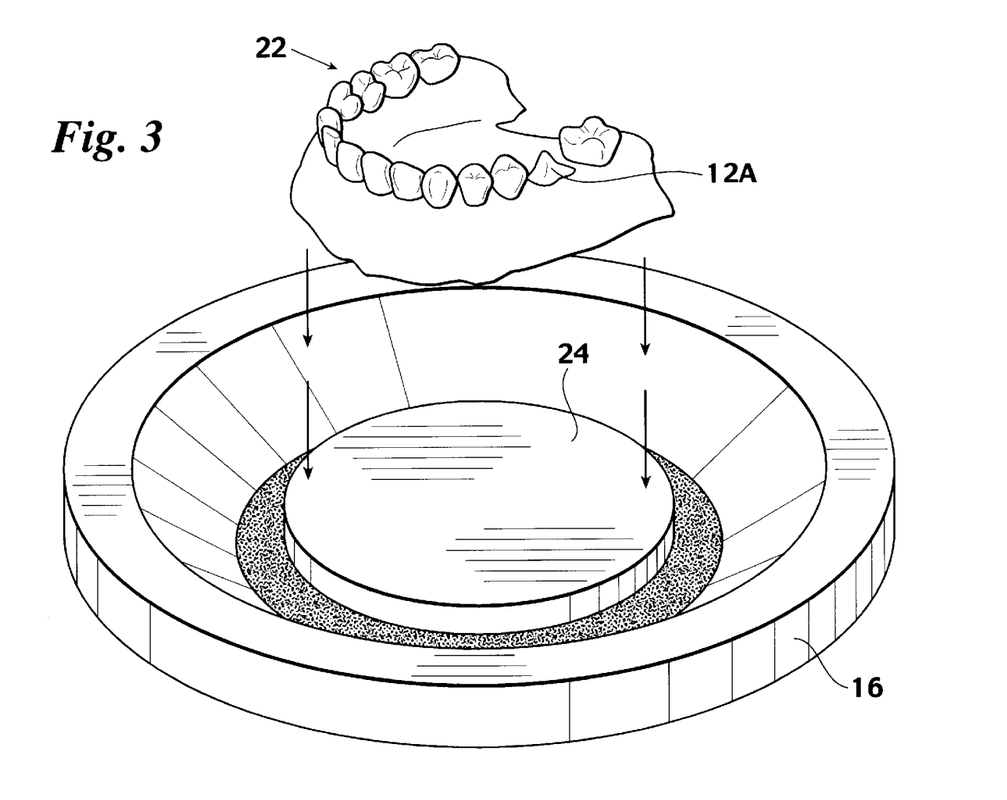
FIG. 3 illustrates a second model of the patient's teeth after the tooth to receive a crown has been prepared by a dentist. The model is made from an impression and is positioned on a platform within a container by which heat and pressure is applied to a plastic film to encapsulate the model.

After the dentist has prepared the natural tooth to receive a crown, a second impression is made, not shown in the drawings, and from the second impression, a second model is made, such as of plaster, the second model being indicated by the numeral 22 in FIG. 3. The second model shows the configuration of the tooth to receive the crown, the model of the prepared tooth being indicated by the numeral 12A.

Figure 4:
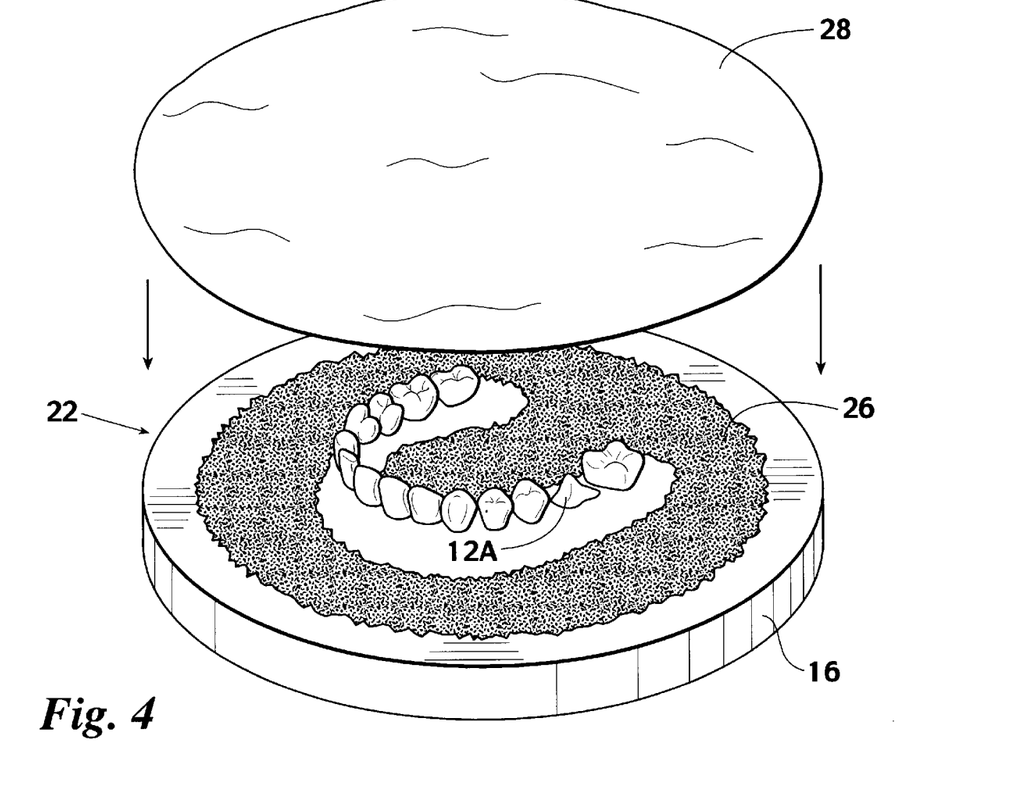
FIG. 4 shows the second model ready to receive a thin plastic foil by the application of heat and air pressure.

Second model 22 is shown in FIG. 3 as it is placed on a platform 24 of form making apparatus 16. FIG. 4 shows second model 22 positioned within the form making apparatus 16. To fill up space around the model so that the resulting form more successfully contours the model the empty space is filled with a granular material 26 as seen in FIG. 4 and also in FIG. 1. The granular material is commonly used in the equipment for making plastic forms but is not directly involved in the invention.

Figure 5:
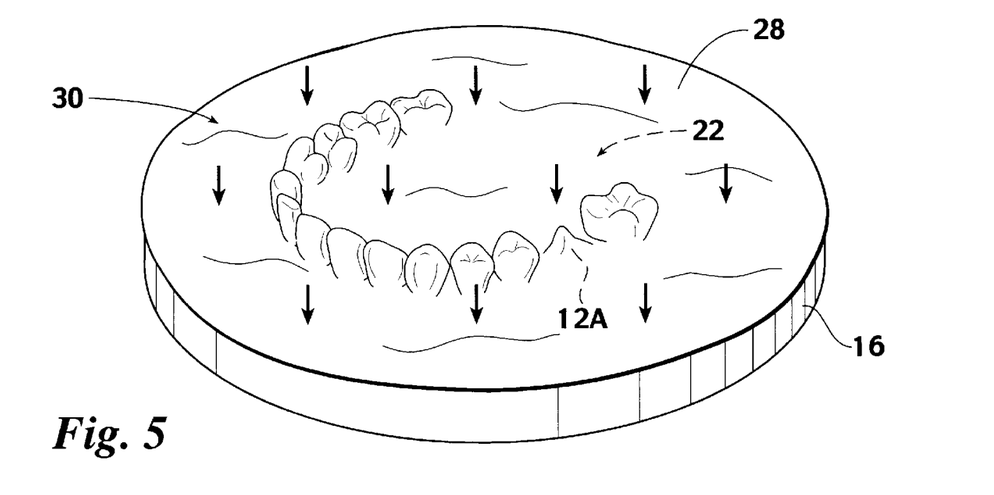
FIG. 5 shows the second model covered by a thin plastic sheeting that is of the characteristic that ceramic material does not adhere to it.

FIG. 4 shows the placement of a disk of thin, plastic foil 28 over the second model 22 which, by the application of heat and air pressure is forced to closely conform to the exterior of the second model as illustrated in FIG. 5. Plastic foil 28 is commercially available from Scheu-Dental and sold under the trademark "ISOFOLAN". It does not bond to acrylic or to ceramic forming molding compositions used herein.

The steps as illustrated in FIG. 4 and 5 result in encapsulating the teeth of second model 22 with a thin ceramic releasing film. The film encapsulated model is indicated by the numeral 30 in which the model of the prepared tooth 12A is encapsulated by film 28.

While the procedures of treating first model 10 in FIGS. 1 and 2 and that of treating second model 22 in FIGS. 3 and 4 are essentially the same, they are carried out for entirely different purposes. FIGS. 1 and 2 illustrate the procedure for creating a form 22 that will be used later in the process, the form being used to define the exterior configuration of the crown. The processes of FIGS. 3 and 4 is to provide a foil covering over second model 22 and particularly over tooth 12A to be crowned. The reason that the plastic covering is required as illustrated in FIGS. 3 and 4 is to achieve a surface over the model of the tooth to be crowned to which ceramic forming material does not adhere.

Figure 6:
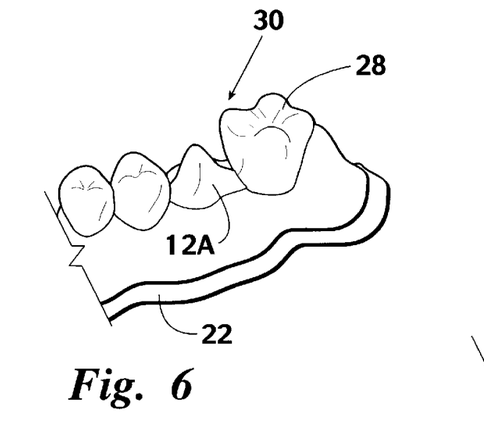
FIG. 6 shows a portion of the film covered second model.

After the plastic film covering has been applied to the second model as illustrated in FIG. 3, the dentist is ready to form the crown that will be used to apply to the patient's prepared tooth. A summary of important steps in the sequence of steps for making a crown is illustrated in FIGS. 6 through 11. FIG. 6 shows a broken away portion of model 22 with plastic foil 28 thereon. FIG. 6 is essentially the second model 22 as shown in FIG. 5 with the thin plastic foil securely conformed to it to provide the film encapsulated model 30. However, FIG. 6 shows only a fragmentary portion of second model 22. In practicing the invention, the first and second models 10 and 22 are best maintained as initially formed, that is, where the model typically includes the entire upper or lower teeth of the patient, however, FIGS. 6 through 11 show only fragmentary portions of second model 22 to simplify the illustrations. While the first and second models are typically maintained in tact, the plastic foil after having been conformed to the shape of the models may be trimmed away to include only the portion encompassing the tooth to be crowned and the teeth adjacent to it. Trimmed away portions of the plastic foil forms are shown in FIGS. 6 through 11.

As previously indicated, FIG. 6 shows second model 22 having the tooth 12A sculptured in the shape to receive a crown and the tooth, including the teeth adjacent to it, encapsulated in a plastic foil 28 for the sole purpose of providing a surface to which ceramic forming material will not adhere. The plastic foil 28 encapsulating second model 22 as illustrated in FIG. 6 is not employed to change the shape of the crown to be formed and therefore the film is as thin as possible. If the second model could be manufactured of a material to which ceramic material does not adhere, then the use of plastic foil 28 would not be required, however, no such practical model making material is known at this time.

Figure 7:
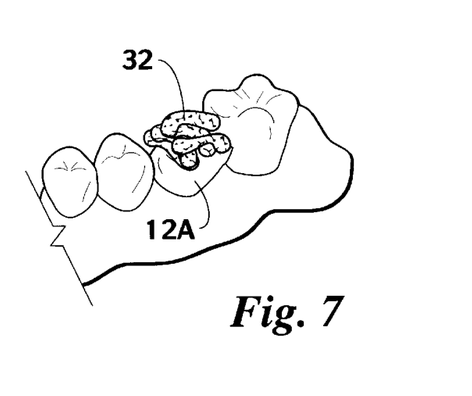
FIG. 7 shows placing on the prepared tooth of the plastic foil encapsulated second model crown forming material, such as a moldable polymer glass ceramic.

FIG. 7 shows the foil encapsulated crown as seen in FIG. 6 but with moldable ceramic forming material 32 applied to the foil covered prepared tooth 12A. Ceramic forming material 32 is preferably a polymer-glass moldable ceramic that is commercially available in a plastic state and that can be hardened to a ceramic solid by the application of ultraviolet light. The ceramic forming material 32 is manually placed on prepared tooth 12A in sufficient quantity to form the required crown.

Figure 8:
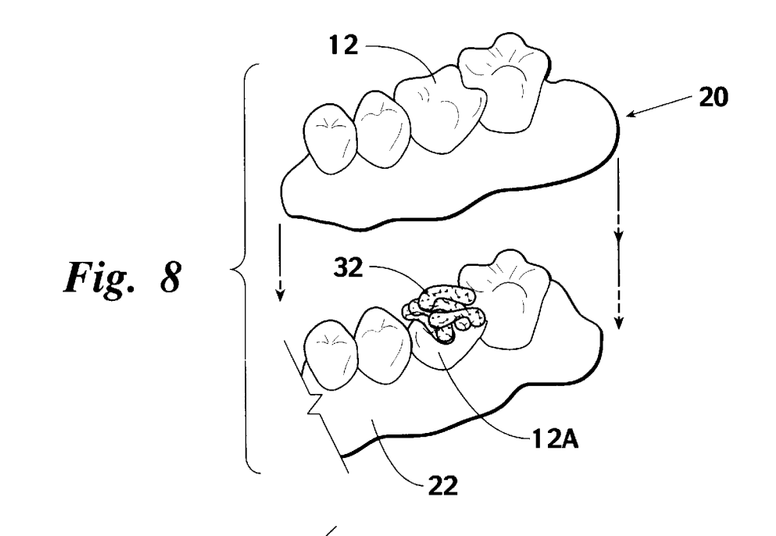
FIG. 8 is an exploded view showing the film encapsulated second model having ceramic forming plastic material thereon as shown in FIG. 7 and shows the external crown form obtained in FIG. 2 to be placed down over the film covered second model.

FIG. 8 shows the step of inserting a trimmed away section of form 20 obtained in the process illustrated in FIGS. 1 and 2, that is, the form 20 is cut away from the plastic foil 18 after it has been conformed by heat and pressure to the exterior of the first model that includes a sculptured configuration of tooth 12 having a form of the exterior configuration of the crown. Thus, the form 20 has the desired exterior configuration of the crown whereas the foil encapsulated model 30 provides the interior or concave configuration of the crown. When form 20 is pressed down over the film encapsulated model 30, ceramic forming material 32 takes an exterior shape defined by form 20 and an interior shape defined by foil encapsulated model 30.

Figure 9:
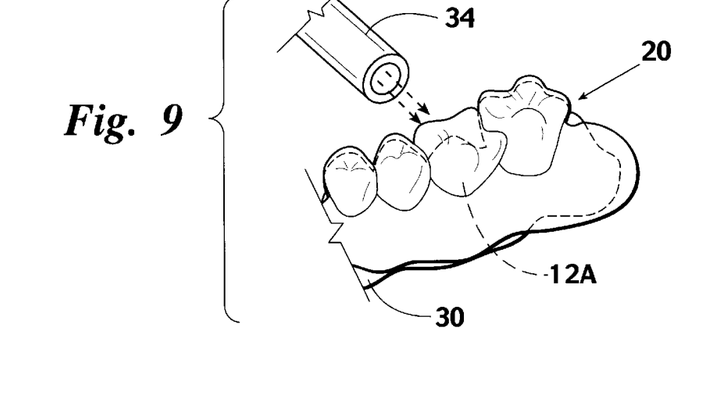
FIG. 9 shows the form obtained in FIG. 2 pressed down over the film covered second mold to cause the plastic ceramic forming material to conform to both the interior and exterior configuration of the desired crown and shows the application of ultraviolet light to solidify the crown forming material.

FIG. 9 shows form 22 pressed down over foil encapsulated model 30 to press the ceramic forming material 32 into the desired shape of the crown. An ultraviolet light source 34 is then placed adjacent to ceramic forming material 32 surround the prepared tooth to solidify it.

Figure 10:
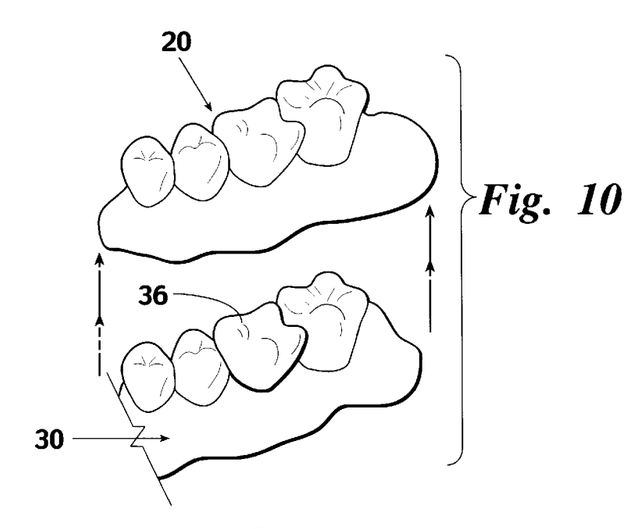
FIG. 10 is an exploded view showing the form removed from the foiled covered second model and shows the crown having been formed as a result of the solidification or curing of the crown forming material.
Figure 11:
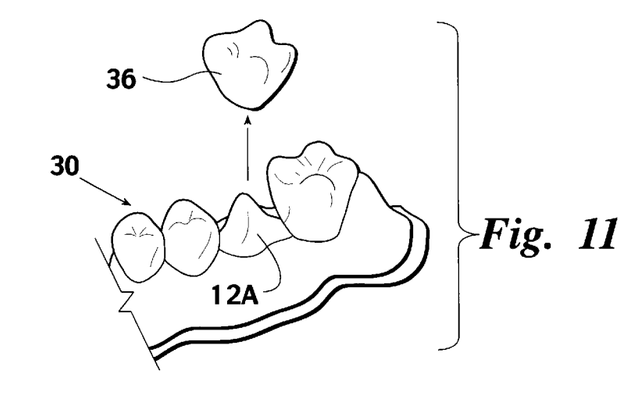
FIG. 11 shows the created crown being removed from the film covered second model. The crown is ready to have any surplusage ground away from it and then polished so that it is in condition to be cemented onto the prepared tooth of the patient.
Figure 12:
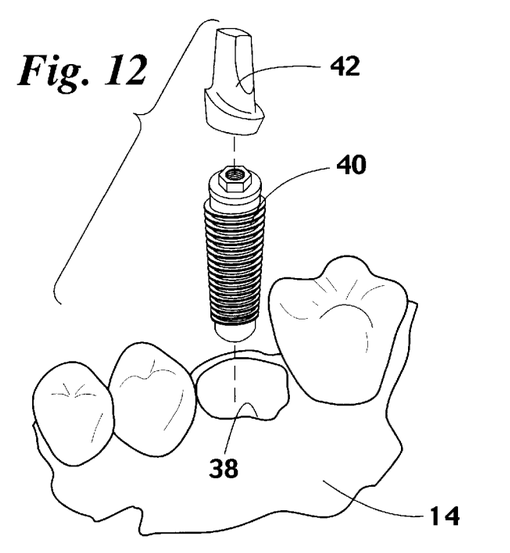
Figure 13:
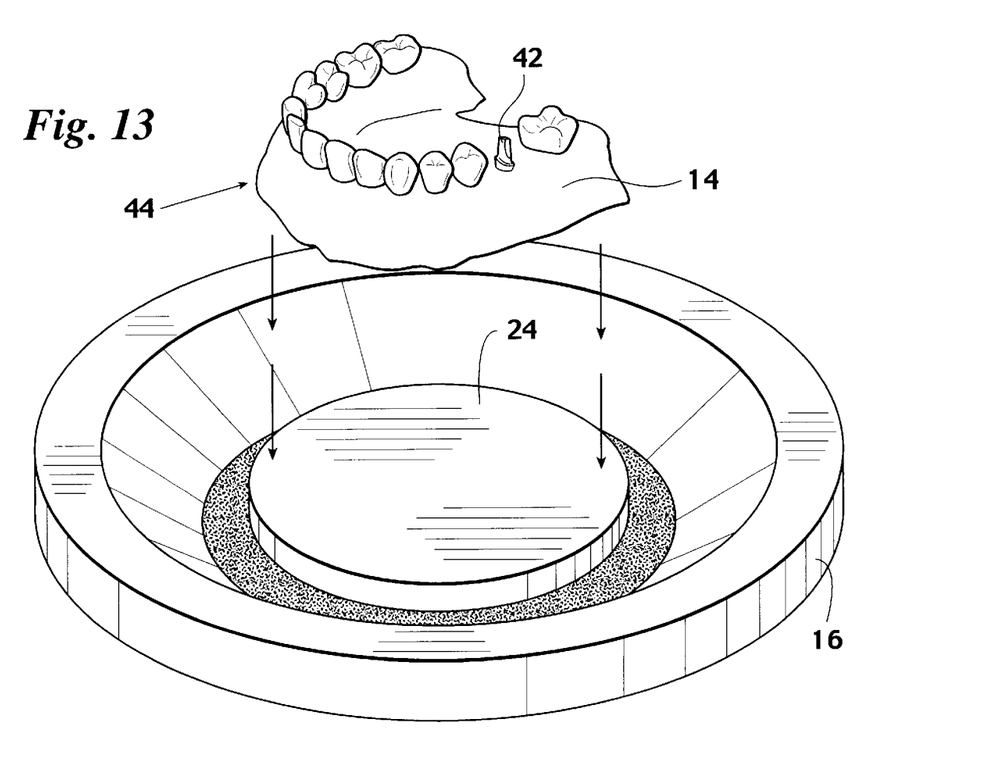
Figure 14:
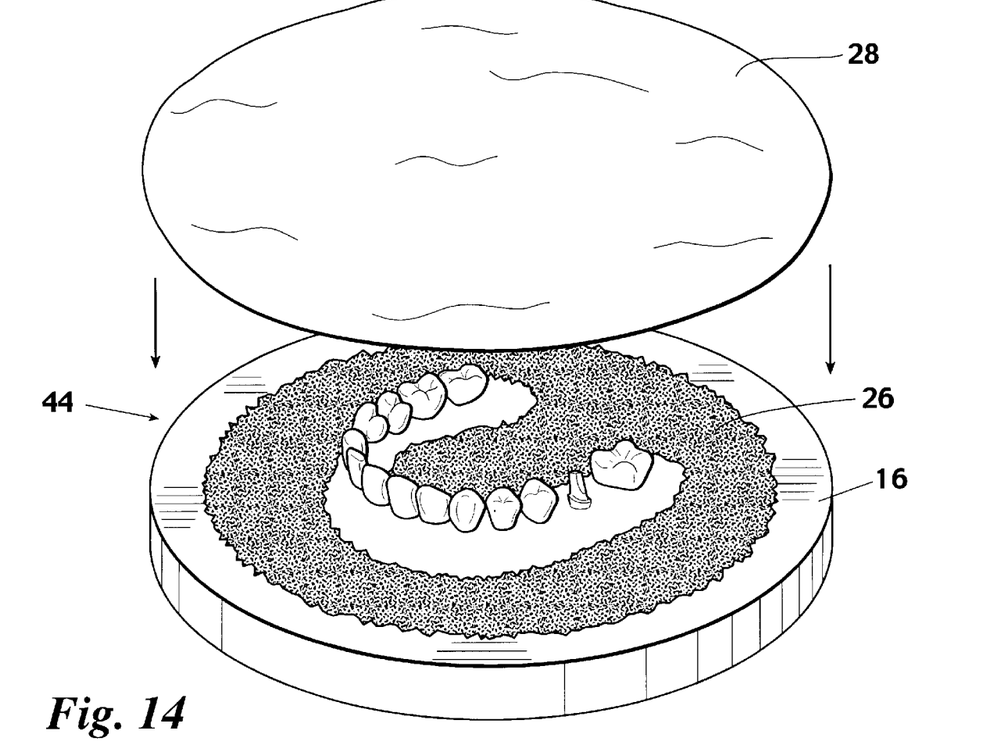
Figure 15:
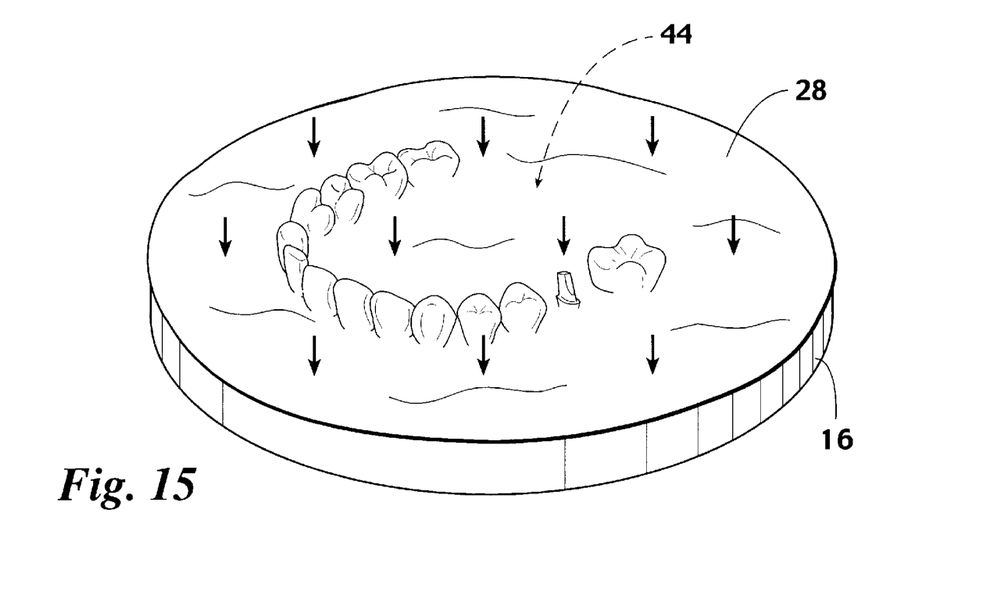
Figure 16:
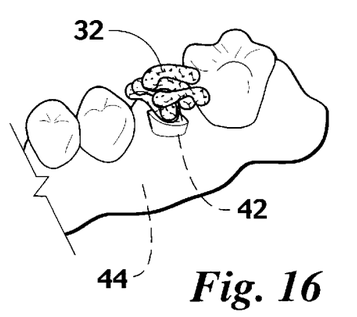

After the ceramic forming material has solidified, form 20 is removed from the film encapsulated model 30 as illustrated in FIG. 10, leaving the hardened crown 36 which, as illustrated in FIG. 11, can be removed from film encapsulated model 30. Thus, the crown 36 has been completed. If, when form 20 is removed from film encapsulated model 30 crown 36 remains within the confines of form 20 the form can be cut away, being no longer required, to extract the crown. In any event, the crown 36 is removed as a separate, created element which the dentist can then finish for use for cementing onto the patient's prepared natural tooth. Crown 36 as formed by this process may require the removal of extraneous ceramic forming material which can be done by grinding away any surplusage. The crown 36 can be polished and subjected to final hardening processes, such as by subjecting the crown to more intense and prolonged exposure to ultraviolet light as necessary to insure that the crown forming material has reached its desired degree of hardness.

Crown 36 is then ready for cementing into position on the patient's prepared tooth 12A in exactly the same way as a crown having been produced by a laboratory. However, the entire procedure as described herein can be consummated within a dentist office. The procedure thus eliminates the necessity for applying a temporary crown to the patient's prepared tooth while a permanent tooth is being prepared. Further, many of the steps in the procedure can be done by dental technicians in the dentist office. The trained skill of the professional dentist is particularly required for structuring for the tooth to receive a crown, for applying sculpturing material to the tooth to be crowned as replicated in the first mold, the final shaping and polishing of the finished crown 36 and cementing the crown onto the patient's prepared tooth. Many of the other steps can be accomplished by a trained assistant.

The steps illustrated and described herein are the essential steps and in the actual practice of the procedures secondary steps may be employed to facilitate formation of a superior crown. For instance, FIGS. 7 and 8 show the deposition of ceramic forming material 32 onto the film covered prepared tooth 12A, followed by positioning form 20 down over the film encapsulated model to force the plastic ceramic forming material to take the desired shape followed by the application of ultraviolet light as shown in FIG. 9. In actual practice, it may be necessary to place layers of the ceramic forming material 32 onto the film covered prepared tooth 12A and hardened the inner layers using ultraviolet light with only the final outside layer of the ceramic forming material 32 being on the tooth 12A when form 20 is applied over it so that the desired external shape of the crown is obtained. The reason for placement of the ceramic forming material in layers is that this material hardens most effectively when it is of a relatively shallow depth since ultraviolet light loses intensity when it penetrates the material and therefore the ceramic forming material can be more successfully hardened when done in stages.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A method of installing a replacement of a patient's deteriorated tooth comprising the steps of:
   (1) making an impression of the patient's teeth including at least the portion thereof including the deteriorated tooth that requires replacement;
   (2) by use of the impression obtained in step (1) making a first model that replicates the patient's teeth including at least the portion thereof having the deteriorated tooth to be replaced;
   (3) applying sculpturing material as necessary to the deteriorated tooth to be replaced as replicated in said first model obtained in step (2) to obtain a prepared first model having a sculptured tooth with the desired appearance of a crown for use in replacement of the deteriorated tooth;
   (4) placing plastic foil over said prepared first model obtained in step (3);
   (5) heating and pressuring said plastic foil to cause it to conform to said prepared first model to obtain an external crown form;
   (6) removing said external crown form from said prepared first model;
   (7) extracting from the patient's jaw the deteriorated tooth;
   (8) installing a dental post in the area of the patient's jaw from which said deteriorated tooth has been extracted;
   (9) making an impression of the patient's teeth including at least the portion thereof including said dental post;
   (10) by use of the impression obtained in step (9), making a second model that replicates the patient's teeth including at least the portion thereof having said dental post;

(11) placing a thin plastic foil over said second model as obtained in step (10);

(12) heating and pressuring said thin plastic foil to cause it to conform to and encompass said post as replicated in said second model;

(13) placing moldable crown forming material on the plastic foil encapsulated dental post portion of said second model;

(14) placing the external crown form obtained in step (6) over said foil covered second model to cause said moldable crown forming material thereon to take an external contour matching the shape of said prepared tooth and an internal contour matching the shape of said post;

(15) hardening the moldable crown forming material to cause the creation of a crown;

(16) removing the crown from off of said foil covered second model and out of said external crown form;

(17) removing any surplusage from the crown obtained from step (16) and polishing the crown to provide a prepared crown; and (18) cementing the prepared crown onto said dental post.

2. A method of installing a replacement for a patient's deteriorated tooth according to claim 1 wherein step (15) is carried out employing ultraviolet light.

3. A method of installing a replacement for a patient's deteriorated tooth according to claim 1 wherein said moldable crown forming material employed in step (13) is a polymer glass ceramic.

4. A method of installing a replacement for a patient's deteriorated tooth according to claim 1 wherein step (13) is carried out in more than one stage by first placing a layer of moldable crown forming material on said plastic foil encapsulated prepared tooth of said second model, at least partially hardening the layer followed by the application of an additional layer or layers, the final layer remaining in a plastic state to receive step (14) whereby the external contour of the crown forming material will match the shape of the sculptured tooth obtained in step (3).

5. A method of installing a replacement for a patient's deteriorated tooth according to claim 1 wherein said dental post is in two parts including a distal base portion mounted within the jaw bone of the patient and a proximal mounting portion attachable to said distal base portion, said crown being configured to and cementable to said proximal mounting portion.

6. A method of replacing a missing tooth of a patient comprising the steps of:

(1) making an impression of the patient's teeth including at least the portion thereof including the space from which a tooth is missing;

(2) by use of the impression obtained in step (1) making a first model that replicates the patient's teeth including at least the space from which the tooth is missing;

(3) cementing a replacement tooth form in said first model to fill in the space of the missing tooth to obtain a prepared first model including a replicated missing tooth;

(4) placing plastic foil over said prepared first model obtained in step (3);

(5) heating and pressuring said plastic foil to cause it to conform to said prepared first model to obtain an external crown form;

(6) removing said external crown form from said prepared first model;

(7) installing a dental post in the area of the patient's jaw from which a tooth is missing;

(8) making an impression of the patient's teeth including at least the portion thereof including said dental post;

(9) by use of the impression obtained in step (8), making a second model that replicates the patient's teeth including at least the portion thereof having said metal post;

(10) placing a thin plastic foil over said second model as obtained in step (9);

(11) heating and pressuring said thin plastic foil to cause it to conform to and encompass said post as replicated in said second model;

(12) placing moldable crown forming material on the plastic foil encapsulated dental post portion of said second model;

(13) placing the external crown form obtained in step (6) over said foil covered second model to cause said moldable crown forming material thereon to take an internal contour matching the shape of said dental post and an external contour matching the shape of said replicated missing tooth obtained in step (3);

(14) hardening the moldable crown forming material to cause the creation of a crown;

(15) removing the crown from off of said foil covered second model and out of said external crown form;

(16) removing any surplusage from the crown obtained from step (16) and polishing the crown to provide a prepared crown; and (17) cementing the prepared crown onto said dental post.

7. A method of replacing a missing tooth of a patient according to claim 6 wherein step (14) is carried out employing ultraviolet light.

8. A method of replacing a missing tooth of a patient according to claim 6 wherein said moldable crown forming material employed in step (12) is a polymer glass ceramic.

9. A method of replacing a missing tooth of a patient according to claim 6 wherein step (12) is carried out in more than one stage by first placing a layer of moldable crown forming material on said plastic foil encapsulated prepared tooth of said second model, at least partially hardening the layer followed by the application of an additional layer or layers, the final layer remaining in a plastic state to receive step (13) whereby the external contour of the crown forming material will match the shape of the sculptured tooth obtained in step (3).

10. A method of replacing a missing tooth of a patient according to claim 6 wherein said dental post is in two parts including a distal base portion mounted within the jaw bone of the patient and a proximal mounting portion attachable to said distal base portion, said crown being configured to and cementable to said proximal mounting portion.

* * * * *